United States Patent
Jeffer

[11] Patent Number: 5,885,077
[45] Date of Patent: *Mar. 23, 1999

[54] METHODS OF ANCHORING DENTURES OVER CROWN COPINGS AND POST ABUTMENTS

[75] Inventor: Peter H. Jeffer, New York, N.Y.

[73] Assignees: Austenal, Inc., Chicago, Ill.; Nu-Dent, Inc., New York, N.Y.

[*] Notice: The term of this patent shall not extend beyond the expiration date of Pat. No. 5,678,993.

[21] Appl. No.: 899,019

[22] Filed: Jul. 23, 1997

Related U.S. Application Data

[63] Continuation-in-part of Ser. No. 408,597, Mar. 22, 1995, Pat. No. 5,678,993, which is a continuation-in-part of Ser. No. 233,849, Apr. 26, 1994, Pat. No. 5,513,998.

[51] Int. Cl.$^6$ .................................................. A61C 13/02
[52] U.S. Cl. ........................................................ 433/168.1
[58] Field of Search .............................. 433/167, 168.1, 433/169, 170, 171, 172, 173, 174, 175, 176, 177

[56] References Cited

U.S. PATENT DOCUMENTS 3,618,213  11/1971  Shepherd et al. .
4,619,891  10/1986  Takahashi .
4,670,480   6/1987  Morrone .
4,705,836  11/1987  Ohtsuka et al. .
5,268,396  12/1993  Lai .
5,306,338   4/1994  Tsunekawa .
5,338,190   8/1994  Tregillis .
5,431,563   7/1995  Huybrechts .

*Primary Examiner*—Nicholas D. Lucchesi
*Attorney, Agent, or Firm*—Wallenstein & Wagner, Ltd.

[57] ABSTRACT

A known elastomeric non-methyl methacrylate soft material has been used as a soft denture liner material. The material includes powder and liquid components which are mixed together and cured. The invention involves lining an underlying surface of an acrylic overdenture, wherein the overdenture is applied over a crown coping over a tooth or over a post with a ball or hour-glass shaped abutment. A liner is formed having the characteristics of being flexible, resilient, shape retentive, hydrophobic, soft, spongy and cushiony. A known sealer component is then applied over the liner to create a non-absorbent exterior surface seal and glaze. By varying the powder to liquid ratio, the material can be made more dense thus hardening or softening it for various applications. By removing the exterior surface and roughening the material, it can easily be adjusted, repaired or refurbished. The material allows for a quick cure or a dental laboratory processed cure and is compatible for either chair-side or laboratory use.

13 Claims, 3 Drawing Sheets

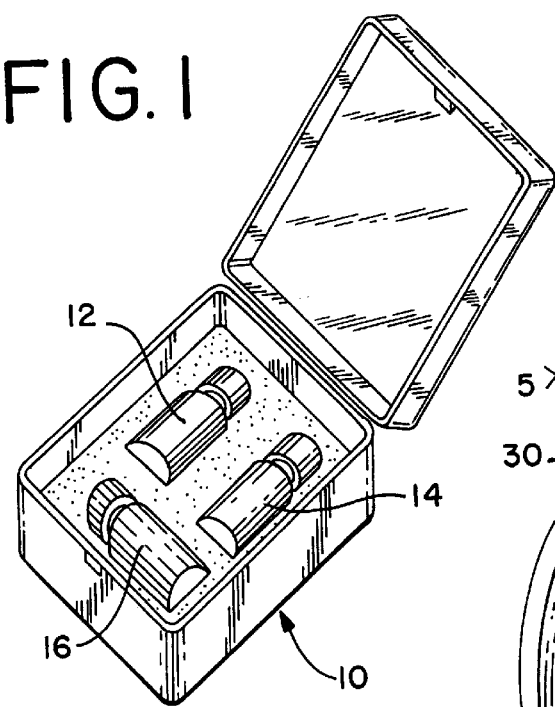
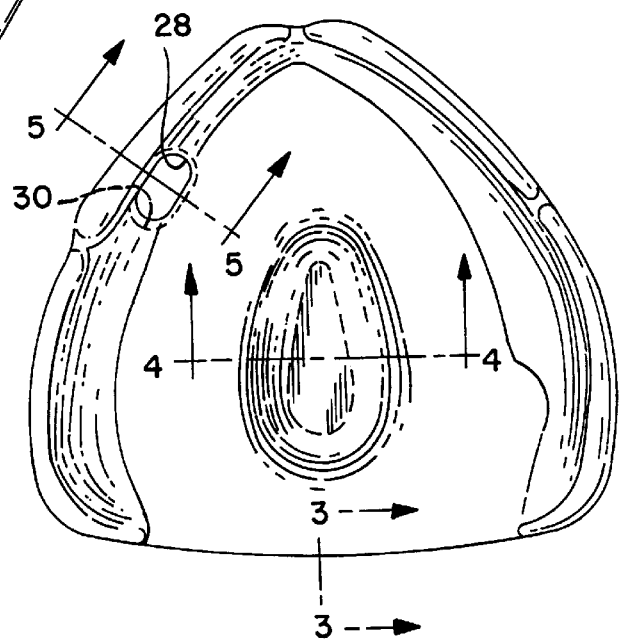
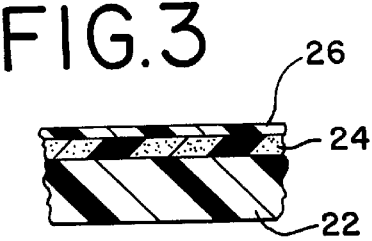
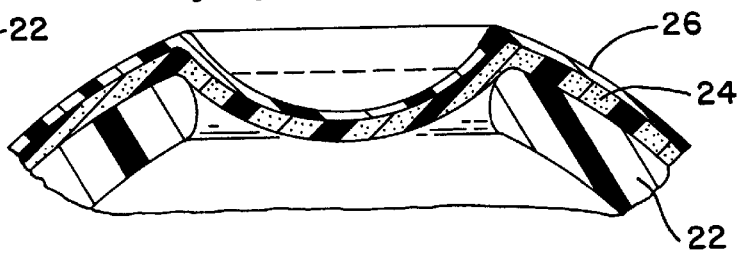
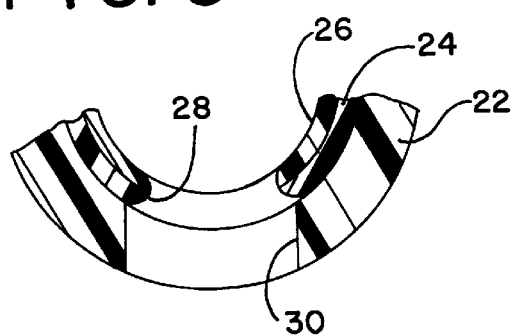
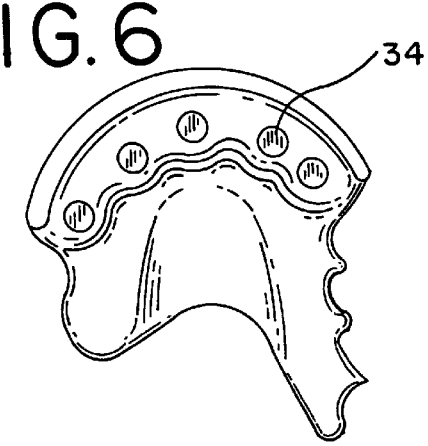

FIG. 9
FIG. 11
FIG. 12
FIG. 13
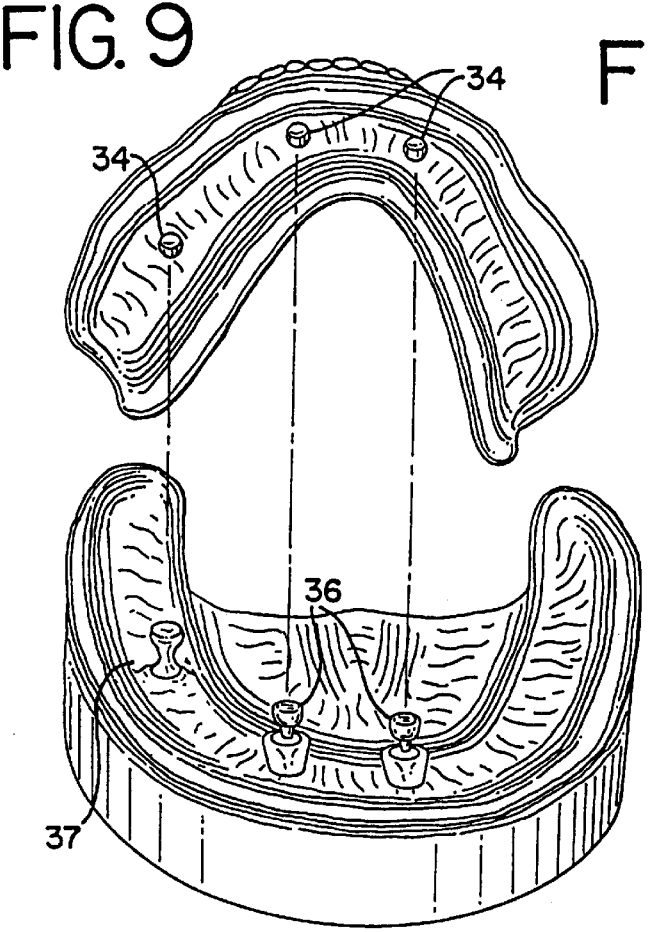
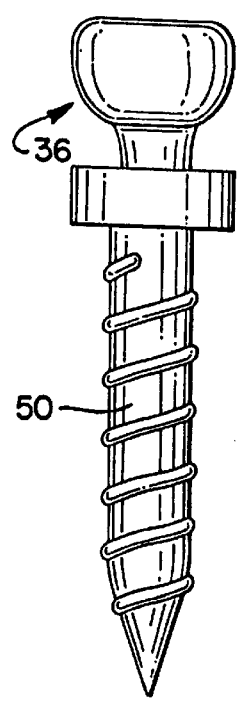
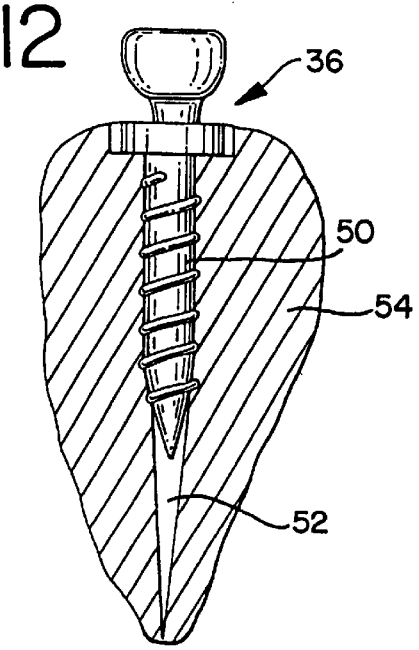
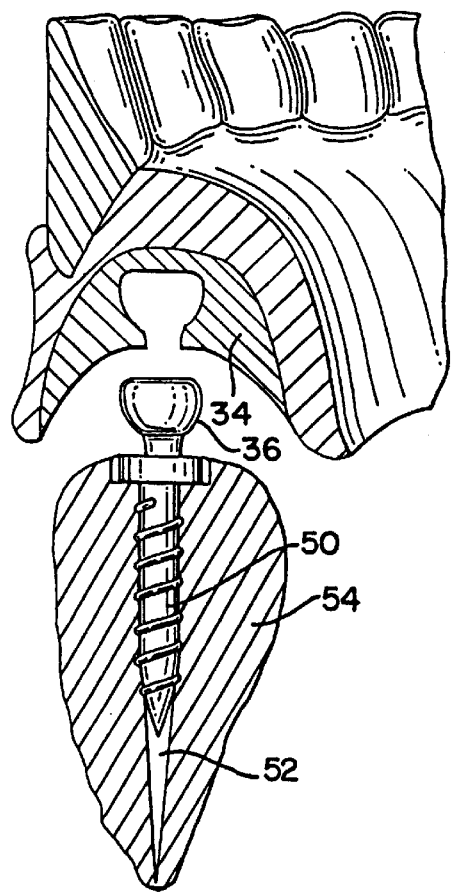

METHODS OF ANCHORING DENTURES OVER CROWN COPINGS AND POST ABUTMENTS

RELATED APPLICATIONS

The present application is a continuation-in-part of application Ser. No. 08/408,597, filed Mar. 22, 1995, now U.S. Pat. No. 5,678,993, which is a continuation-in-part of application Ser. No. 08/233,849, filed Apr. 26, 1994, now U.S. Pat. No. 5,513,988, issued May 7, 1996.

TECHNICAL FIELD

The present invention generally relates to clinical uses of soft denture liner materials and in particular to new and novel clinical uses of a known elastomeric non-methyl methacrylate soft denture liner material.

BACKGROUND OF INVENTION

For decades, restorative dentists and dental product manufacturers have attempted to develop a soft liner for dentures and prosthetic devices addressing the various short term and long term clinical challenges presented by partially and fully edentulous patients. Examples of long term uses of soft denture liners may be indicated where the patient has undercuts caused by severe alveolar ridge resorption; anatomical voids requiring obturators; anatomical growths such as palatal tori; and, knife edge alveolar ridges. Examples of short term uses of soft denture liners include overdentures supported by implants or teeth; post-surgical prosthodontic situations that require interim lining while both soft and hard tissue heal; and, gasket like connectors and liners over and around existing teeth.

Various types of soft denture liners exist in the art which are intended for short term or long term service. Soft denture liners are known in the art which are laboratory-processed and intended as long term liners, such as include Molloplast-B™ (Buffalo (Dental). Also known in the art are chairside-processed soft liners intended for short term service. These include Lynal™ (L.D. Caulk/Dentsply) and Visco-Gel™ (Ash/Dentsply). Until the methods of the present invention were developed, no soft denture liner was known that was chairside or laboratory-processed and intended for short, intermediate and long term clinical use.

In addition, prior art liners have different problems associated with their clinical applications. In particular, silicon soft liner materials must be "glued" onto the hard acrylic surface with an adhesive bonding agent, and often this bonding agent contains a methyl methacrylate monomer. These self-curing adhesives leach into the soft material and harden it.

Moreover, adhesives harden and crack at the "seam," or junction where the soft material is glued on to the hard acrylic. Lactic acid, alcohol, and/or medication accelerate this separation. At this point, bacteria, fungus, odor, debris, and stain penetrate the soft liners. This natural absorption degrades the soft liners creating a hardening, peeling, as well as chemically and physiologically unstable condition.

In addition, the repair process of other existing materials is difficult since the base material either flakes off when trimmed, or it cannot be re-molded with standard dental tools. Also, to "glue" small sections of liner onto thin acrylic edges is difficult or impossible as the liners break off under the constant pressure which occurs in the oral cavity.

There are various products which use heat or light to cure resins of various formulation onto prosthetic devices. Almost all of these formulations require a bonding agent which runs into the same problems as mentioned above. Many of these finished liners absorb liquids accelerating their deterioration.

Another category of liners which are temporary in nature are known as "tissue conditioners". These gels or stick-on resins last only weeks or a few months before they peel-off. They usually are soft due to high porosity, and thus they absorb liquids which ultimately breakdown the materials. The absorbency allows bacteria and odor buildup in the mouth creating an undesirable situation.

Hence, prior to the development of the present invention, a need existed for clinical techniques using a non-methyl methacrylate soft liner material capable of remaining soft during intermediate to long term service and is chairside or laboratory compatible.

SUMMARY OF THE INVENTION

The clinical methods and techniques of the present invention use a known elastomeric material which overcomes many of the disadvantages of prior art liner materials. This material is a non-methyl methacrylate soft material which effectively fuses to acrylic surfaces or to itself without a gluing agent. The present invention is based upon the recognition that the known elastomeric non-methyl methacrylate soft material described above could be used in permanent lining techniques heretofore not practiced in the prior art. Thus, while the prior art used such material as a reline material for dentures it was not previously recognized that the attributes of that material made it particularly useful for other dental techniques. It was also not previously recognized that the curing characteristics inherent in the material made it possible to apply the material at chairside to cure, for example, in only five minutes in the patient's mouth, although other conventional methods of curing may be used. The characteristics of the elastomeric non-methyl methacry-late material make it particularly suitable for diverse applications as a long lasting, soft, hydrophobic, cushion-like material chemically bonded onto any acrylic surface.

The known liner material used in the clinical techniques of the present invention is formed by blending a powder component of polyethylmethacrylate and a liquid component of Di-n-butyl phthalate, ethyl acetate and ethyl alcohol which are mixed together until all of the powder particles are totally moistened. It has been discovered and is an element of the present invention that softness of the material can be varied for each clinical use and may be varied for each patient as well. The softness or hardness of the material is dependent upon varying the powder to liquid ratio. The ratio of powder to liquid may vary within the range of 2:1 for softer material to 3:1 for harder or denser material. The resultant mixture is then applied onto dentures by being spatulated on the denture surface or is formed in various shapes and configurations depending upon the given clinical application. A polyvinyl chloride/polyvinyl acetate copolymer dissolved in a methyl ethyl ketone solvent forms a sealer component which is then applied over the liner to create a nonabsorbent, moisture impervious surface seal and glaze.

The objects of this invention are clinical techniques and applications for intermediate and long term service of the above noted non-methyl methacrylate material. These techniques generally include using the material to form (1) linings of gaskets over an anchor device protruding from tissues such as implant attachments or posts, implanted into the root of a tooth; (2) gaskets over ball abutments and hader bars; and, (3) linings of gaskets around an anchor device protruding from tissue such as a crown coping over an existing teeth.

Other advantages and aspects of the invention will become apparent upon making reference to the specifications, claims, and drawings to follow.

BRIEF DESCRIPTION OF THE DRAWINGS

FIG. 1 is a perspective view of a kit for packaging the materials used in the methods of this invention;

FIG. 2 is a plan view of a denture having the liner of the materials applied thereto;

FIGS. 3–5 are cross-sectional views taken through FIG. 2 along the lines 3—3, 4—4 and 5—5, respectively;

FIG. 6 is a bottom plan view of the material over the tissue and healing caps;

FIG. 9 is an exploded view of a denture having sockets lined using a method of the present invention to receive ball abutments and a crown coping over a tooth;

FIG. 11 is a side view of a post with a ball abutment;

FIG. 12 is a side view of a post embedded in the root of a tooth; and,

FIG. 13 is a side view of a post embedded in the root of a tooth where the ball abutment is aligned for emplacement in a denture.

DETAILED DESCRIPTION

Figure 7:
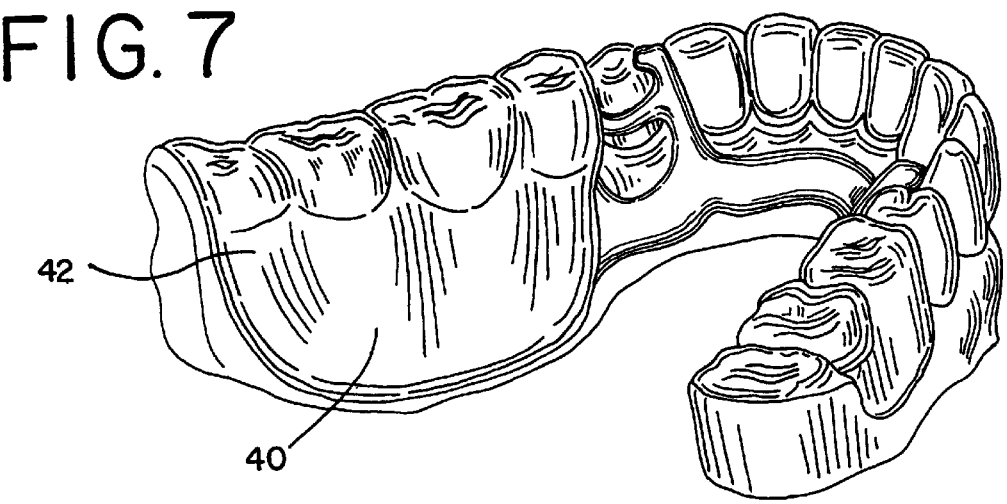
FIG. 7 is a perspective of a removable partial denture having a distal extension formed by the materials of the present invention.

While this invention has the capability of being employed in many different forms, there is shown in the drawings and will herein be described in detail a preferred embodiment of the invention with the understanding that the present disclosure is to be considered as an exemplification of the principles of the invention and is not intended to limit the broad aspect of the invention to the illustrated usages.

The characteristics of the elastomeric non-methyl methacrylate denture liner material used in the clinical techniques of the present invention make it particularly suitable for diverse applications as a long lasting, soft, hydrophobic, cushion-like material which chemically bonds onto any acrylic surface without need of a gluing agent. The material may be processed at chairside or in the laboratory using a hot water cure. The material fuses to acrylic by cross linking into the exterior pores thus establishing a chemical and mechanical bond. The material remains spongy soft, flexible, shape retentive, and permanently attached to the underlying hard material.

The liner material used in the present invention is formed by blending a powder component comprised of a polyethylmethacrylate, and a liquid component comprised of a mixture of Di-n-butyl phthalate, ethyl acetate and ethyl alcohol. The liquid component and the powder component are slowly mixed together until all of the powder particles are totally moistened. Essential to the methods of the present invention is the degree of softness of the material for a given clinical use. The softness or hardness of the material is dependent upon varying the powder to liquid ratio. For example, where more powder is used a more dense material results which in turn is harder. Variations of powder to liquid may be within the range from 2:1 for softer material to 3:1 or more for harder material.

The various components of the material can conveniently be prepackaged in a kit. FIG. 1, for example, illustrates such a kit 10 which could take any suitable form, for example, a carton in which the components would be packaged. Thus, as shown therein a bottle or container 12 could be used for a powder component while a liquid component could be packaged in a bottle 14. A sealer would be packaged in bottle or container 16. In the practice of most of the methods of the present invention, three parts of loosely packed powder from container 12 is mixed into one part of liquid from container or bottle 14 slowly stirring until all powder particles are thoroughly saturated.

Powder component in container 12 would be polyethylmethacrylate while the liquid component in bottle 14 would be Di-n-butyl phthalate, ethyl acetate and ethyl alcohol solution. The sealer in container 16 would be a polyvinyl chloridepolyvinyl acetate copolymer dissolved in a methyl ethyl ketone solvent component which would be capable of providing a none absorbent surface seal and glaze when applied over the mixture of the cured powder and liquid component.

Sealer 26 as disclosed in the drawings can air dry in two minutes establishing a hydrophobic, non-absorbent, high-gloss, stain resistant, surface finish. This step is repeated for a stronger external bond. No other soft line product uses such a sealer.

The finished soft lined surface will remain soft for multiple years, even in the oral cavity. The use of the sealer 26 effectively prevents lactic acids, bacteria, fungus and other substances from penetrating the hydrophobic soft liner. Thus, internal degradation does not occur as the sealer 26 keeps out all oral fluids.

Since no methyl methacrylate or bonding agent is used in this procedure, the leeching of methyl methacrylate into the soft material does not occur keeping the liner softer for a longer period of time. The specific method of mixing, application, and curing in hot water (under 25 PSI of pressure if desired) accelerates the set of the soft material. The tolerance of temperature extends from 125° F. up to 165° F. so as not to warp the acrylic denture, and the pressure can vary from 15 PSI to 40 PSI for the same results.

Clinical uses of the liner material employed in the methods of the present invention is best disclosed with reference to the following examples.

EXAMPLE I

LINING OF FULL DENTURES AND LINING DENTURE PASS-THROUGH GASKET HOLES SURROUNDING EXISTING TEETH OR ANCHOR DEVICES

Figure 8:
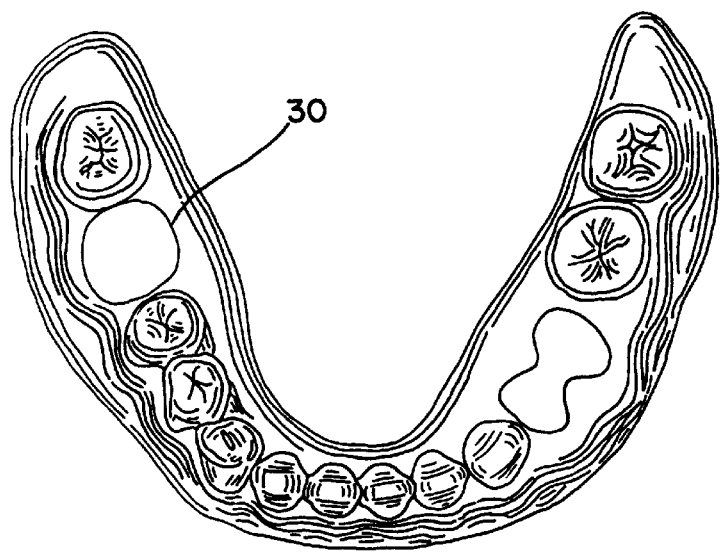
FIG. 8 is a plan view of a denture having pass-through opening to form a gasket around existing teeth in which the gasket edge is lined according to the present invention.

The methods of the present invention may be used to form a lining on the underside of full dentures to improve denture wear, cushion and fit. In addition, as disclosed in FIGS. 2, 5 and 8 a method has also been developed to use the liner material disclosed herein for gasket anchoring. This could be done for retention of a denture as a gasket around the circumference of a pass-through hole. The material can be as a gasket retentive liner 28 bonded the circumference of a hole 30 (such as in FIGS. 2 and 5) and onto the acrylic surfaces to anchor the denture to patient's existing teeth.

FIGS. 2 and 5 disclose using the liner for retention of a denture as a gasket 28 around the circumference of a pass through hole 30 for existing teeth. The hole 30 is enlarged to the desired size. Then the material is blended over, under and around the gasket hole 30, and onto surrounding acrylic surfaces 22. The following chairside technique is preferably used to apply the lining material either as a full denture reline or in lining gasket pass-through holes:

1. Relieve undercuts, grind (1–2+)mm of space to receive material hollowing out entire tissue side of denture to allow room, especially where gum ridge peaks; Roughen peripheral roll & (3+)mm onto outer surface of denture; Clean & dry denture where reline applied;
2. Pour powder, (all at once), into a plastic mixing cup of liquid in a volume ratio of 3 parts powder into 1 part liquid; Gently mix until all the powder particles are moistened; The mixture consistency instantly turns "sticky" or "honey-like"; (Slightly more liquid thins the mix, increases working time, and makes a slightly softer reline);
3. Immediately, generously spatulate and spread the sticky mixture of material evenly onto totally dry denture surface;
4. Patient moistens lips with tongue as this material will not adhere to any saliva or wet covered areas; Insert the denture filled with material into patient's mouth; Have the patient close gently into occlusion for 1 to 1½ minutes;
5. Remove denture from the mouth; Blend and taper excess material with finger coated with material liquid to completely overlap the peripheral roll (3+)mm onto acrylic surface. (Immediately cure);
6. Place denture in cup with relined side up, add steaming hot water (from 125° F. to 165 degrees F.) for (10) minutes;
7. Chill finished relined denture in cold water to temporarily harden soft liner; Remove excess flash with finishing stone or acrylic bur tapering reline on the labial and buckle surface; Finish with a large rubber point, and wet rag wheel & pumice, if desired; High gloss not necessary;
8. Apply a complete coat of sealer with brush or cotton tip applicator over the totally dry material soft liner; Material forms a non-absorbent, high gloss, stain resistance exterior surface; Sealer air dries in (2+) minutes—then, repeat with a second complete coating and allow to dry. A third coating on non-retention area is acceptable.

An advantageous property of the material are its curing characteristics. For example, as previously noted the material can be cured in 10 minutes in steaming hot water, at chairside or in a jig. Alternatively, the material could be cured in 45 minutes in a flask or in only 5 minutes in the mouth for small, thin area relines.

EXAMPLE II

LINING OVERDENTURES FOR IMPLANT HEALING CAPS, BALL ABUTMENTS, CROWN COPING OVER TEETH AND HADER BARS

FIG. 11 discloses a post 50 with a ball abutment 36. The post 50 is screwed into the root 52 of a tooth 54, as shown in FIG. 12. FIG. 13 illustrates the alignment of the ball abutment 36 in the overdenture 34 while the post 50 is embedded in the root 52 of a tooth 54.

FIG. 6 discloses the reline material used in overdentures for implant healing caps 34 and, as disclosed in FIG. 9, in lining overdentures to receive a crown coping over a tooth 37, ball abutments 36 or other anchor devices protruding from the tissue surface. FIG. 6 discloses five healing caps 34. The coating of the cured material with the sealer provides a non-absorbent exterior surface so as to maintain overdenture softness, and prevent discoloration, odor and bacteria ingress. No other polyethylmethacrylate resin uses this technique at the dentist's chairside or in the operatory or in the dental laboratory.

Where the material of the present invention is used immediately after initial surgery to install implants as an implant overdenture soft liner, the load of powder to liquid is varied to form a softer material, usually in the range of 2 to 1. When the material is used to stimulate and cushion healing caps during transitional healing stages after surgery, the load of powder to liquid is varied to form a slightly harder material, usually in the range of 2.5 to 1. When the material is used to enhance anchoring over a crown coping over a tooth or ball abutments, as disclosed in FIG. 9, then a proportion of 3 to 1 is preferred. In either clinical use the following steps would be practiced:

1. Trim back and relieve the tissue side of temporary denture with any acrylic bur to allow for unobstructed seating initially over the tissue area, and again reline over the healing cap(s) when exposed;
2. Pour material powder, (all at once) into liquid in a volume ratio of 2 to 3 parts powder into 1 part liquid; Gently mix until all the powder particles are moistened; Consistency instantly turns "sticky" or "honey-like"; (Slightly more liquid thins the mix, increases working time, and makes a slightly softer reline);
3. Immediately, spatulate the sticky mixture of material into the dry tissue side of the denture previously reamed-out in Step (1); For large surface relines follow step 4a; For small surface relines and for relines over healing cap(s), when exposed, follow step 4b;

4a. Seat over tissue area; patient gently closes into centric occlusion for (1) minute; remove denture; taper and blend excess material with finger coated with material liquid to overlap the peripheral roll (3+)mm onto outer acrylic surface; Immediately, process in steaming hot water, (up from 125° F. to 165 degrees F.) for (10) minutes;

4b. Seat over tissue area, and over healing cap(s), when exposed; Have patient close gently into centric occlusion for in-the-mouth cure in (5) minutes for thin, small area relines; Can also cure in steaming hot water in (10) minutes for larger volume relines.

5. Post curing, chill finished reline in cold water to temporarily harden soft liner. Trim excess material using finishing stone, acrylic bur and large rubber point. Finish with a wet rag wheel & pumice for a smooth surface;
6. Apply two complete coats of Sealer over totally dry reline to form a non-absorbent, high-gloss surface, Sealer air dries in (2+) min., and repeat with a second coat to repel fluids, bacteria, odor and stain. A third coating over non-retentive areas is acceptable.
7. For rebonding, adjustments, and refittings the previously noted chairside techniques would then be used.

The above procedure creates a soft liner on the tissue side of a denture during the transitional healing period after installation of an implant. Due to the softness of the material it creates a light functional load system for moderate vertical stress during osseointegration of the implant cylinder into the jaw bone. Increasing the powder ratio makes material denser or harder, thus allowing for incremental loading. The hardest concentration of powder allows for extended use as a gasket to anchor prosthetic devices onto various fixed implant attachments.

EXAMPLE III

LINING OVERDENTURES FOLLOWING SURGICAL PLACEMENT OF IMPLANTS

Due to the ability to vary the liner's degree of softness, the material is well suited to aid in the progressive healing process following the surgical placement of implants. Specifically, one or two weeks following the implant placement, the tissue side of the overdenture is lined for a soft, light load. A powder to liquid load of approximately 2 to 1 is preferred. After suture removal, the suture line or indentation is blocked with dry foil or suitable material and relined following the technique disclosed in Example I above. The soft material must not interfere with the healing site or the newly-formed flap. The soft liner cushions tender areas and provides a hygienic, non-absorbent surface.

After an appropriate implant integration phase, a second application of soft liner is applied to the tissue side to cushion and anchor onto the healing caps. A powder to liquid load of approximately 2.5 to 1 is preferred. This healing cap overdenture enables a gradual healing load with light functional stimulus to the implant. This thin area reline will cure in the mouth in approximately five (5) minutes.

After attachment of the ball abutments or the bar connectors, the overdenture is relined to form a gasket over the balls or bars without O-rings or clips. A powder to liquid load of approximately 3 to 1 is preferred. This soft liner will absorb torque pressures and provide retention for long term service with easy adjustment.

EXAMPLE IV

FORMING OVERLINERS FOR ANATOMICAL GROWTHS AND DENTURE INSERTS FOR ANATOMICAL VOID

Figure 10:
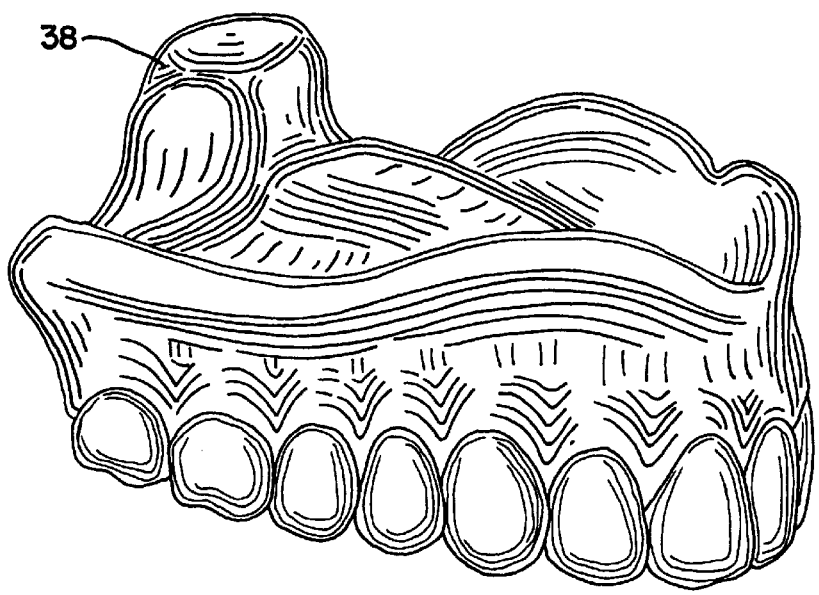
FIG. 10 is an upper denture wherein an obturator to fill an anatomical void is formed using a method of the present invention.

Given that the material used in the methods of the present invention bonds onto itself, clinical techniques have been developed to form overliners for anatomical growths as well as forming obturators and other inserts for anatomical voids. FIGS. 2 and 4 disclose use of the material for extension over large voids 32 on denture surfaces for use in palatal tori. Though the recommended peripheral roll formed from the material should have a height of between 1.5 to 3 mm, the material can be molded to one inch or more to form an obturator 38 for patients with cleft palates as disclosed in FIG. 10. When covering anatomical growths or filling anatomical voids, a load of approximately 2.5 to 1 to form a softer finished product is preferred.

EXAMPLE V

GASKETS OVER EXISTING TEETH

A softer load as described in Example IV may be used to attach acrylic stents onto existing teeth to prevent teeth grinding. This material can also be used to gasket onto existing teeth inside of a mouth guard for retention and cushioning or inside of a stent as part of a medication delivery system. For example, a stent formed to extend below the gingival margin may retain and dispense topical medication along the gingival tissue. The material is capable of this clinical application because of its capacity to gasket onto teeth while containing the medication for time release dispensing.

EXAMPLE VI

FORMING DISTAL EXTENSION FOR REMOVABLE PARTIAL DENTURES

As disclosed in FIG. 7 the material can be used to stabilize a partial denture by molding a flange or saddle area 40 to the residual ridge 42. The material allows saddle area 40 to grip undercuts, contours to muscle form and alveolar ridges to help anchor partial dentures. The prior art uses hard acrylics for the saddle having a lower peripheral edge which is both sharp and uncomfortable. In contrast, the soft extensions of the present invention allow the saddle areas 40 to flex during denture insertion or removal. Once in place, the saddle areas 40 return to their original position. In addition, as bone absorption flattens existing ridge configurations, this material cushions, anchors, and stabilizes dentures onto the changing ridge structure. Thus, the material takes full advantage of the underlying undercuts while providing the comfort of a soft cushion base.

For a removable partial denture to accommodate the soft liner material used in the methods of the present invention, approximately 2–3 millimeters of relief is necessary under the denture saddle to allow for a minimum of 1 millimeter of hard acrylic and 1–2 millimeters of soft liner material. Preferably a proportion of 2.5 parts powder component to 1 part liquid component is used.

After blending the powder component and the liquid component, the resultant material is formed over the peripheral roll of the denture onto the surrounding acrylic surface, for more surface contact and thus a better and more permanent chemical bond. The lack of a seam at the junction where the soft reline is bonded onto the hard acrylic prevents separation of the soft material from the hard acrylic.

EXAMPLE VII

MAINTENANCE OF DENTURES

The soft liner material used in the present invention can be trimmed using standard dental tools; and, it rebonds to itself for fast, simple repairs at chairside or in a dental laboratory. Re-sealing of the exterior surface should be initiated once per year which extends the longevity of service from intermediate to long term. To reseal, (1) the existing surface sealer is ground off, (2) the surface is smoothed, (3) the surface is dried, and (4) two new coats of sealer are painted on.

While the invention has been described with reference to a preferred embodiment, it will be understood by those skilled in the art that various changes may be made and equivalents may be substituted for elements thereof without departing from the broader aspects of the invention. Also, it is intended that broad claims not specifying details of a particular embodiment disclosed herein as the best mode contemplated for carrying out the invention should not be limited to such details.

We claim:

1. A method of lining an underlying surface of an acrylic overdenture, wherein the overdenture is applied over a crown coping over a tooth, the method using a non-methyl methacrylate soft liner material, the material including a powder component of polyethylmethacrylate and a liquid component being an admixture of Di-n-butyl phthalate, ethyl acetate and ethyl alcohol, the method comprising the steps of:

blending 3 parts powder component into 1 part liquid component;

forming an elastomeric material by mixing the powder component into the liquid component until all of the powder component is thoroughly moistened; and, applying the elastomeric material to the underlying surface of the overdenture.

2. The method of claim 1 further including the step of:

applying a sealer over the exterior surface of the liner to create a non-absorbent exterior surface seal and glaze.

3. The method of claim 2 wherein the sealer includes a polyvinyl chloride/polyvinyl acetate copolymer dissolved in a methyl ethyl ketone solvent.

4. A method of lining an underlying surface of an acrylic overdenture, wherein the overdenture is applied over a post with a ball abutment, the method using a non-methyl methacrylate soft liner material, the material including a powder component of polyethylmethacrylate and a liquid component being an admixture of Di-n-butyl phthalate, ethyl acetate and ethyl alcohol, the method comprising the steps of:

forming a first elastomeric material by mixing approximately 3 parts powder component into approximately 1 part liquid component until all of the powder component is thoroughly moistened; and applying the first elastomeric material to the underlying surface of the overdenture.

5. The method of claim 4 wherein the overdenture is applied over the post approximately 1 to 2 weeks following placement of the post.

6. The method of claim 4 further including the step of:

applying a sealer over the exterior surface of the liner to create a non-absorbent exterior surface seal and glaze.

7. The method of claim 6 wherein the sealer includes a polyvinyl chloride/polyvinyl acetate copolymer dissolved in a methyl ethyl ketone solvent.

8. The method of claim 4 further comprising the steps of:

forming a second elastomeric material by mixing approximately 2.5 parts powder component into approximately 1 part liquid component until all of the powder component is thoroughly moistened; and, applying the second elastomeric material to the underlying surface of the overdenture.

9. The method of claim 8 further including the step of:

applying a sealer over the exterior surface of the liner to create a non-absorbent exterior surface seal and glaze.

10. The method of claim 9 wherein the sealer includes a polyvinyl chloride/polyvinyl acetate copolymer dissolved in a methyl ethyl ketone solvent.

11. The method of claim 8 further comprising the steps of:

forming a third elastomeric material by mixing approximately 3 parts powder component into approximately 1 part liquid component until all of the powder component is thoroughly moistened; and, applying the third elastomeric material to the underlying surface of the overdenture.

12. The method of claim 11 further including the step of:

applying a sealer over the exterior surface of the liner to create a non-absorbent exterior surface seal and glaze.

13. The method of claim 12 wherein the sealer includes a polyvinyl chloride/polyvinyl acetate copolymer dissolved in a methyl ethyl ketone solvent.

* * * * *